(12) United States Patent
Smith et al.

(10) Patent No.: US 10,131,874 B2
(45) Date of Patent: Nov. 20, 2018

(54) CELL CULTURE SUPPORT AND ASSOCIATED METHOD FOR CELL GROWTH AND RELEASE

(71) Applicant: General Electric Company, Schenectady, NY (US)

(72) Inventors: Reginald Donovan Smith, Schenectady, NY (US); Prameela Susarla, Manvel, TX (US); Slawomir Rubinsztajn, Ballston Spa, NY (US); Brian David Polizzotti, Swampscott, MA (US); Anton Beletskii, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 138 days.

(21) Appl. No.: 15/262,644

(22) Filed: Sep. 12, 2016

(65) Prior Publication Data

US 2016/0376550 A1    Dec. 29, 2016

Related U.S. Application Data

(62) Division of application No. 12/493,331, filed on Jun. 29, 2009, now Pat. No. 9,469,839.

(51) Int. Cl.
*C12N 5/00* (2006.01)
*C08F 293/00* (2006.01)
*C12M 1/26* (2006.01)
*C12M 1/00* (2006.01)
*C08F 8/12* (2006.01)

(52) U.S. Cl.
CPC .............. *C12N 5/0075* (2013.01); *C08F 8/12* (2013.01); *C08F 293/005* (2013.01); *C12M 23/20* (2013.01); *C12M 33/00* (2013.01); *C12N 5/0068* (2013.01); *C12N 2533/30* (2013.01); *C12N 2539/10* (2013.01)

(58) Field of Classification Search
CPC .................................................. C12N 2533/40
USPC ......................................................... 435/396
See application file for complete search history.

(56) References Cited

U.S. PATENT DOCUMENTS

2008/0009063 A1* 1/2008 Okano ................. C12N 5/0068
435/402

\* cited by examiner

*Primary Examiner* — Ruth A Davis
(74) *Attorney, Agent, or Firm* — GE Global Patent Operation; Pabitra Chakrabarti

(57) ABSTRACT

A cell culture support comprising a substrate, and a dual stimuli responsive block copolymer immobilized on the substrate, wherein the dual stimuli responsive block copolymer is both thermoresponsive and pH responsive. A method of culturing cells comprising the cell culture support having a dual stimuli responsive copolymer immobilized on a substrate, wherein the dual stimuli responsive copolymer is thermoresponsive and pH responsive; and growing the cells on the cell culture support. By lowering the temperature, cells are released from the cell culture support.

19 Claims, 12 Drawing Sheets

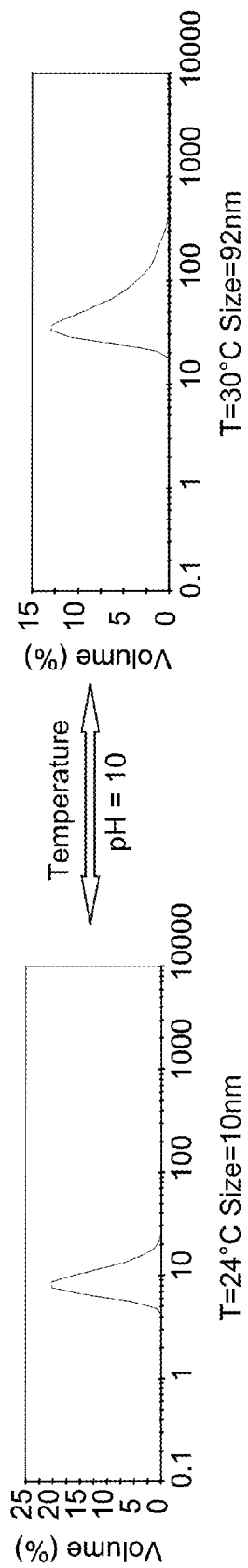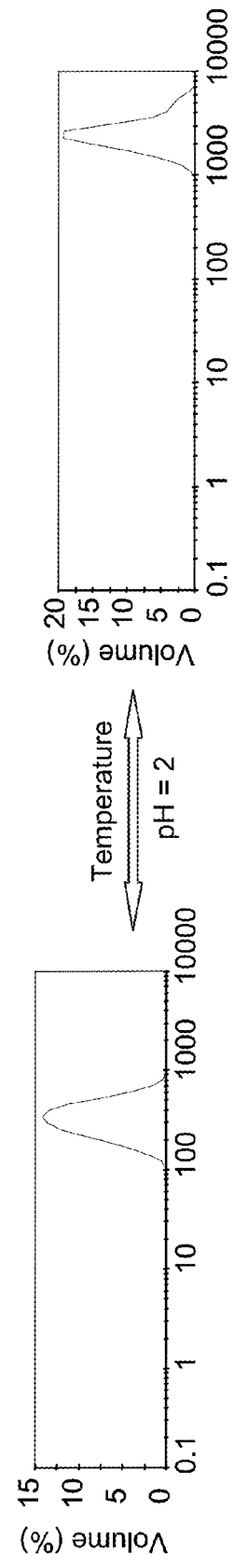

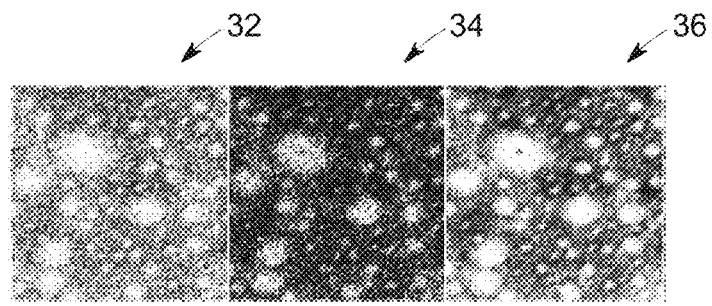
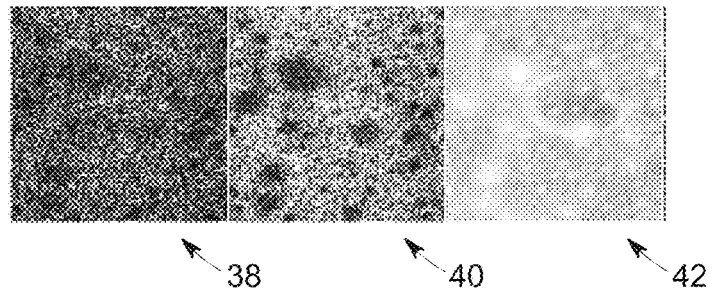
FIG. 7A
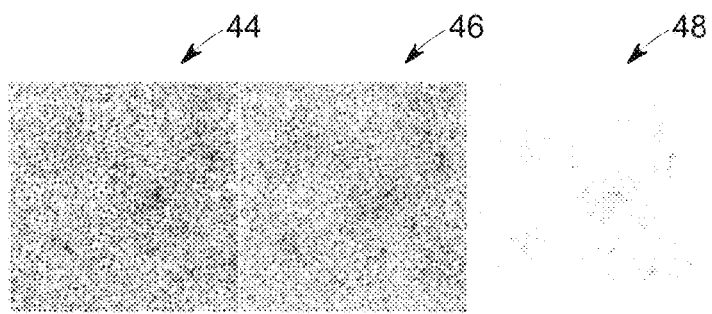
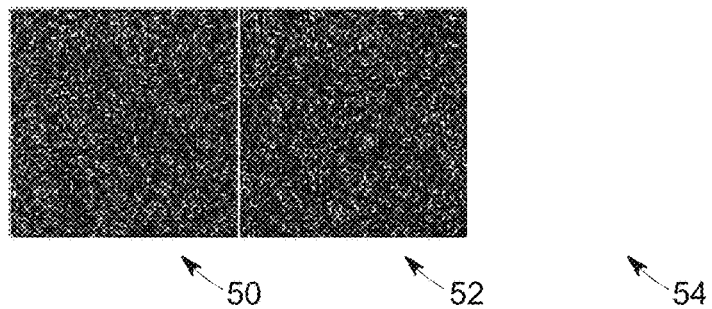
FIG. 7B

FIG. 8A
FIG. 8C
37°C
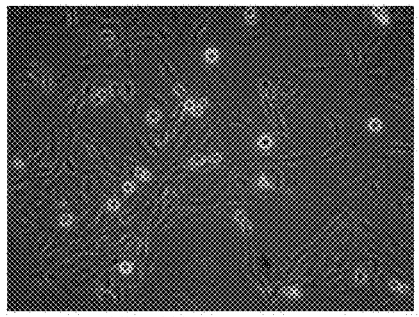
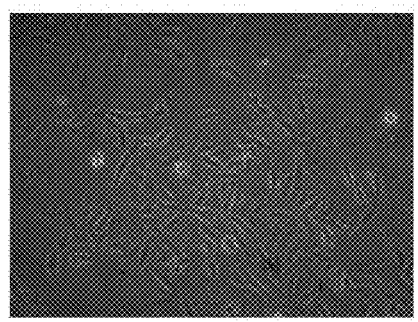
4°C
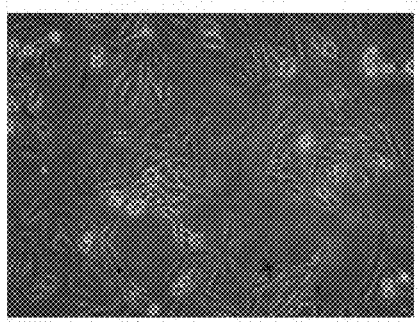
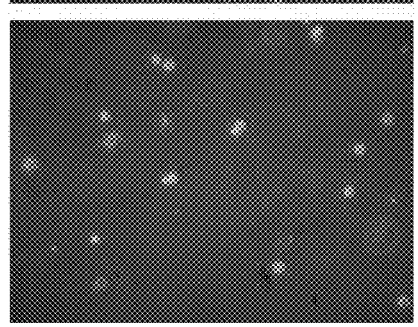
FIG. 8B
FIG. 8D

37°C

4°C

FIG. 11A
FIG. 11C
37°C
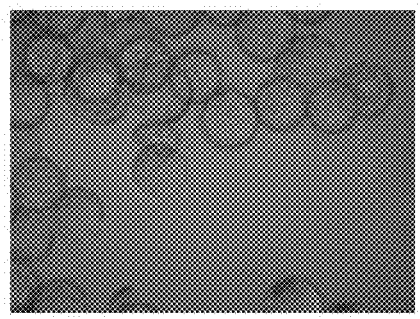
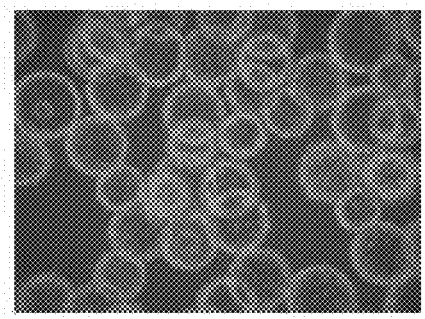
4°C
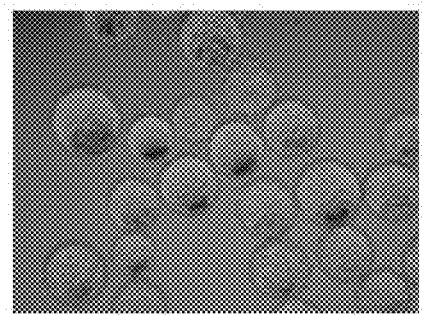
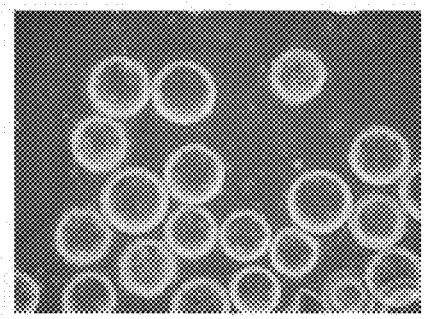
FIG. 11B
FIG. 11D FIG. 12A
FIG. 12C
37°C 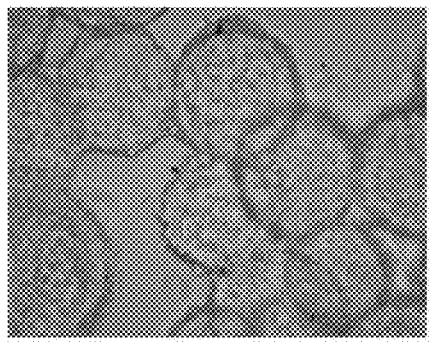 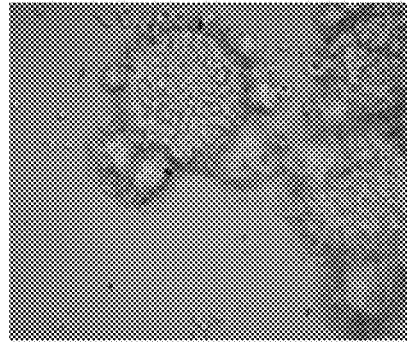
4°C 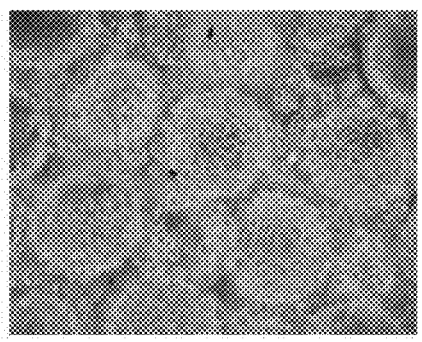 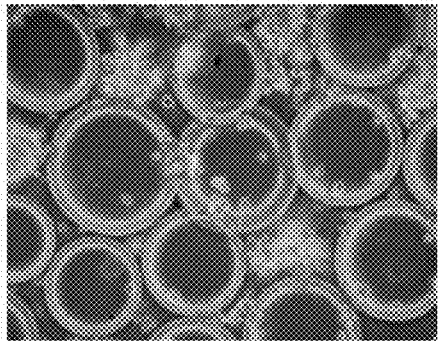
FIG. 12B
FIG. 12D

CELL CULTURE SUPPORT AND ASSOCIATED METHOD FOR CELL GROWTH AND RELEASE

CROSS-REFERENCE TO RELATED APPLICATIONS

This is a Divisional of U.S. patent application Ser. No. 12/493,331, which was filed on Jun. 29, 2009, and entitled CELL CULTURE SUPPORT AND ASSOCIATED METHOD FOR CELL GROWTH AND RELEASE, which is hereby incorporated by reference in its entirety.

FIELD

The invention relates to cell culture support, and associated method for cell growth and release. More particularly, the invention relates to polymer based cell culture support, and associated method for cell growth and release.

BACKGROUND

Adherent cells have conventionally been grown on glass surfaces or on polymer substrates. The surfaces for cell culture are often pre-treated to enhance cell adhesion and proliferation. Flasks, plates, and Petri-dishes are commonly used for cell culture in laboratories. For industrial-scale cell culture, such as in the bioprocess industry, the use of microcarriers for cell attachment and proliferation is common. These microcarriers are typically beads or disks with dimensions in the hundreds of micrometers range.

Cultured cells may be detached or released from cell culture supports by a variety of methods. Commonly used cell release methods comprise mechanical methods (such as scraping), treatment with proteolytic enzymes (such as trypsin), the use of calcium chelators (such as EDTA), or a combination of such methods. However, many of these conventional cell release methods can cause adverse effects on cultured cells, and may modify their inherent structure and function. For example, treatment of cells with trypsin (trypsinization) is a harsh method, and is not desirable for delicate cells such as stem cells, due to its potential effect on cell phenotype. Trypsin is typically derived from animals, and may contain impurities like co-fractionated proteins or biological agents such as viruses and *mycoplasma*. Impurities of animal origin may limit the use of released cells for critical applications such as cell therapy. Mechanical methods of cell release are labor intensive and are impractical for industrial-scale cell culture applications.

Thermoresponsive polymers (TRPs) have recently been used as supports for culturing adherent cells. For example, poly N-isopropyl acrylamide (PNIPAM) has been used as coating for cell culture supports to provide a gentle mechanism for releasing cultured cells. TRPs undergo a sol-to-gel transition when the temperature is raised above lower critical solution temperature (LCST). When the TRP is above its LCST, it forms a collapsed gel or precipitated phase, on which cells can adhere and proliferate. Lowering the temperature of the cell culture system below the LCST stimulates a physical change (swelling/hydration) in the TRP and imparts greater hydrophilicity, which causes a triggered release of the cultured cells. The use of polyelectrolyte-coated TRPs has recently been demonstrated. For example, NIPAM-containing polyelectrolyte multilayer coatings have been used as cell culture supports. These supports were prepared by coating a glass substrate with alternate layers of negatively charged polystyrene sulfonate-co-poly N-isopropyl acrylamide (PSS-co-PNIPAM) and positively charged polyallylamine hydrochloride-co-poly N-isopropyl acrylamide (PAH-co-PNIPAM) copolymers.

Efficient cell release is particularly important for high yield in industrial scale cell culture processes. So, there is an emerging need to develop better cell culture supports for efficient cell attachment and proliferation. Gentle cell release methods to detach the cultured cells from such cell culture supports are also needed.

BRIEF DESCRIPTION

The present invention relates to dual stimuli responsive copolymer coated cell culture support for better cell adhesion, culture, and subsequent release. Embodiments of the present invention include cell culture supports coated with single layer or multi-layer dual stimuli responsive copolymers. Methods for cell culture and cell release are also provided.

In one embodiment, a cell culture support is provided. The cell culture support comprises a substrate, and a dual stimuli responsive copolymer immobilized on the substrate via non-covalent interaction.

In another embodiment, a cell culture support comprises a substrate, and a dual stimuli responsive copolymer immobilized on the substrate via non-covalent interaction. The dual stimuli responsive copolymer is both thermoresponsive and pH responsive.

In yet another embodiment, a cell culture support is provided, wherein the cell culture support comprises a substrate, a first layer immobilized on the substrate via non-covalent interaction, wherein the first layer comprises a polymer and the second layer comprises a dual stimuli responsive copolymer, and the second layer immobilized on the first layer via non-covalent interaction.

In another embodiment, a cell culture support is provided, wherein the cell culture support comprises a substrate, a first layer immobilized on the substrate via non-covalent interaction, wherein the first layer comprises a dual stimuli responsive copolymer and the second layer comprises a polymer, and the second layer immobilized on the first layer via non-covalent interaction In another embodiment, a method of culturing cells is provided. The method comprises the steps of providing a cell culture support comprising a dual stimuli responsive copolymer immobilized on a substrate, growing the cells on the cell culture support and releasing the cells from cell culture support by incubating the cell culture support at a temperature lower than lower critical solution temperature of the dual stimuli responsive copolymer. The dual stimuli responsive copolymer has a lower critical solution temperature in a range from about 10° C. to 37° C. and the dual stimuli responsive copolymer is pH responsive in a pH range from about 3 to 10.

DRAWINGS

These and other features, aspects, and advantages of the present invention will become better understood when the following detailed description is read with reference to the accompanying drawings in which like characters represent like parts throughout the drawings, wherein:

FIGS. 5A to 5D are dynamic light scattering (DLS) graphical plots illustrating the effect of pH and temperature on size distribution of particles or aggregates (measured as hydrodynamic radius).

FIGS. 7A and 7B are two-dimensional ToF-SIMS image analysis of negative ions of an example of a glass slide coated with PLL/TRABC. [Scale: dark—low ion concentration; light—high ion concentration].

FIGS. 8A to 8D are 100× optical microscopy images of slides illustrating cell growth and cell release for CHO cells.

FIGS. 11A and 11C are 40× optical microscopy images of cultured cells (CHO cells) on uncoated or coated cytodex microcarrier beads. FIGS. 11B and 11D are 40× optical microscopy images of uncoated or monolayer of PLL/TRABC coated Cytodex™ microcarrier bead after cell release (for CHO cells).

FIGS. 12A and 12C are 100× optical microscopy images of cultured cells on uncoated or coated cytodex microcarrier beads. FIGS. 12B and 12D are 100× optical microscopy images of the uncoated or coated cytodex microcarrier beads of FIGS. 12A and 12C respectively, after cell release (for CHO cells).

DETAILED DESCRIPTION

Figure 1A:
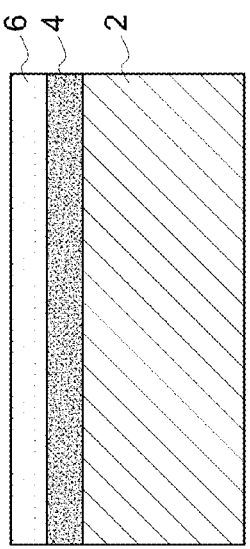
FIGS. 1A to 1D are cross sectional views of glass slides coated with Poly L-Lysine (PLL) or thermoresponsive amphiphilic block copolymer (TRABC) or a combination of both.
Figure 1B:
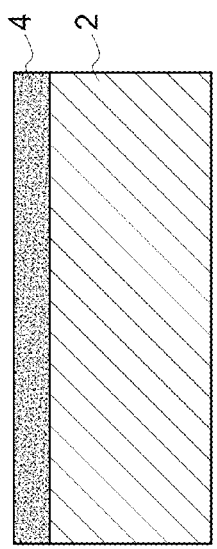

To more clearly and concisely describe the subject matter of the claimed invention, the following definitions are provided for specific terms, which are used in the following description and the appended claims. Throughout the specification, exemplification of specific terms should be considered as non-limiting examples.

The invention relates to dual stimuli responsive copolymer coated cell culture support for better cell adhesion, culture, and subsequent release. Embodiments of the invention include cell culture supports coated with a single layer or multiple layers of dual stimuli responsive copolymers.

In some embodiments, the invention relates to a single or multi-layer coated cell culture support having a substrate and a dual stimuli responsive block copolymer coating on the substrate. This cell culture support is useful for cell adhesion, cell growth and for efficient cell release. A high yield of cells is required in various applications involving cell culture, which can be met by using the cell culture supports of this application. The present invention further includes a method and a kit for culturing cells using the same cell culture support.

A "cell culture support" or "cell culture carrier", as referred to herein, is a support for adhering and culturing cells. The cell culture support may comprise a substrate. The substrate may further be coated or layered with a suitable coating material for cell adherence and proliferation. Suitable coating materials may include, but are not limited to, polymers. The polymers may include, but are not limited to, dual stimuli responsive polymers.

A "substrate", as referred to herein, is a base or a holder, which provides support for a coating. This coated substrate can be used as a cell culture support.

The term "dual stimuli responsive", as referred to herein, and in the context of a cell culture support layer or material, refers to the responsiveness of the layer or material to two different external stimuli. Non-limiting examples of external stimuli are temperature, pressure, pH, ionic strength, electrical charge or combinations thereof. For example, a polymer that is sensitive to a change in temperature and a change in pH may be referred to as a dual stimuli responsive polymer.

The term "block copolymer" as referred to herein, is a copolymer chain, wherein monomer units are arranged in blocks. The block copolymer may be a di-block copolymer, a tri-block copolymer or a multiple-block copolymer. For example, a di-block copolymer may be represented as $(A)_m(B)_n$, wherein A and B are two different monomeric units. The integers m and n represent the respective block lengths of the repeating monomeric units (m and n≥1). A tri-block copolymer may be represented as $(A)_n(B)_m(C)_p$ or as $(A)_m(B)_n(A)_p$, where n, m and p are the respective block lengths of the repeating monomeric units (m, n and p≥1). Or, the copolymer chain can consist of several blocks, with a multitude of repeat units and block lengths.

The term "lower critical solution temperature" as referred to herein, is a temperature of a polymer, below which the polymer and solvent are completely miscible and form a single phase. For example, "the LCST of a polymer solution" means that the polymer is uniformly dispersed in a solution at a specified temperature (i.e. LCST) or lower. The polymer aggregates and forms a second phase when the solution temperature is increased beyond the specified temperature (i.e. LCST).

The term "thermoresponsive polymer", as referred to herein, is a polymer that undergoes a physical change when external thermal stimuli are presented. The polymer may change some of its properties at a particular temperature. One such property may be the solubility of a polymer in a particular solvent. For example, a solution of a TRP may be prepared by solubilizing a TRP in a solvent below the LCST of the TRP, where the solution phase of the TRP is stable. When the temperature of the TRP solution is increased above the LCST, the solution phase may become unstable and a second phase forms. Therefore, the TRPs may become less soluble (more hydrophobic) in the solvent, such as, in water, at a temperature higher than LCST. Changing the pH and the ionic strength may affect the LCST of a TRP.

A non-limiting example of a TRP is poly(N-isopropylacrylamide) (PNIPAM). Under standard conditions of neutral pH and in the absence of ionic species, PNIPAM undergoes a phase transition from soluble to insoluble form at ~32° C. The application of TRPs, especially PNIPAM, has been explored in cell culture and tissue engineering because of its LCST~32° C., which is close to physiological temperature of 37° C. At this temperature, the polymer is hydrophobic, which helps to adhere cells on its surface. When the temperature is lowered to below the LCST, the polymer becomes hydrophilic and swollen, which triggers detachment of the cells.

The term "pH responsive polymer" or "pH sensitive polymer" as referred to herein, is a polymer that can change one or more properties at a particular pH. Such pH responsive or pH sensitive polymers are materials that swell or collapse when the pH of the surrounding medium changes. The solubility of these polymers in a particular solvent may change with change in pH. For example, a polymer may be stable in solution at a particular pH whereas the same polymer may aggregate and precipitate under similar conditions but at different pH.

One embodiment of the cell culture support of this invention comprises a copolymer coating on a substrate. The copolymer may be a block copolymer. The coating may comprise a single layer of block copolymer or may comprise multiple layers of block copolymer. The block copolymer is referred to in the description of this non-limiting embodiment as thermoresponsive amphiphilic block copolymer (TRABC). In some embodiments, the invention relates to a cell culture support having a single or multi layer coating on a substrate where the coating may be dual stimuli responsive copolymer. In some other embodiments, the dual stimuli responsive copolymer is a block copolymer. In a specific embodiment, the dual stimuli responsive block copolymer comprises poly (di (ethylene glycol) methylether methacrylate)-co-poly(acrylic acid). Other non-limiting examples of TRABC include poly (di(ethylene glycol)methylether methacrylate)-co-poly(diethylaminoethyl acrylate) and poly (N-isopropyl acrylamide)-co-poly(vinylpyridine).

The cell culture support comprises a substrate, and a dual stimuli responsive copolymer coating. In one embodiment, the dual stimuli responsive copolymer is a block copolymer, such as for example, a TRABC coating, immobilized on the substrate. In this dual stimuli responsive block copolymer, the dual stimuli are temperature and pH. In addition to the block copolymer coating, the support may further comprise one or more additional layers (eg. homopolymer or copolymer).

The cell culture support may be configured as a cell culture bed, a cell carrier bead, disk or scaffold comprising one or more polymeric layers. Non-limiting examples of substrates include a microcarrier, a membrane, a fiber, a hollow fiber, a capillary, a vessel, a flask, a disc, a bead, a Petri dish, a plate, a fabric, a nonwoven, a nano-fiber mat, a particle, a scaffold or a foam. Examples of substrate materials include, but are not limited to, glass, polymer, metal, ceramic and combinations thereof.

The LCST may be tailored as needed for a given application by selecting, or otherwise modifying, the type of polymer. The useful range of LCST can be determined by the temperature at which a given cell type can grow or otherwise survive. In a specific embodiment, the LCST of poly (di (ethylene glycol) methylether methacrylate)-co-polyacrylic acid or PDEGMA-co-PAA is about 26° C. In some embodiments, the copolymer is thermoresponsive in various temperature ranges. Examples of suitable temperature ranges include, but are not limited to 4° C. to 50° C., 10° C. to 37° C., and 20° C. to 30° C.

The block copolymer is responsive to pH in various pH ranges. Examples of suitable pH ranges include, but are not limited to 3 to 7 (e.g. for materials containing carboxylic acid moiety), 6 to 10 (e.g. materials containing amino-functional moiety), and 2 to 10 (e.g. materials containing carboxylic acid and amino functional moieties).

In some embodiments, the cell culture support may be configured to have alternate layers of a copolymer layer and a polymer layer. In some other embodiments, the cell culture support may be configured to comprise alternate blocks or alternate layers of a copolymer layer and a homopolymer layer. In some embodiments, the alternate layer may be referred to herein as first layer or second layer. The first layer may be immobilized on the substrate via non-covalent interaction. In a non-limiting example, this first layer may be a dual stimuli responsive copolymer. In another example, the first layer may be pH or an ionic strength responsive homopolymer. In a specific example, the first layer consists of homopolymer. In some embodiments, the first layer interacts with the second layer via electrostatic interaction. In a further example, a second layer may be immobilized on the first layer via non-covalent interaction. In one example, the second layer is a homopolymer layer. In another example the second layer may be a dual stimuli responsive copolymer layer. In another example, there may be a third layer and fourth layer, wherein the third layer is immobilized on the second layer via non covalent interaction and the fourth layer is immobilized on the third layer via non covalent interaction. The third layer and fourth layers may be polymers or copolymers.

In some embodiments, the first layer comprises a homopolymer and the second layer comprises a copolymer. The cell culture support can further comprise a third layer wherein the third layer comprises a polymer. In one embodiment, the third layer may comprise a homopolymer. The cell culture support can further comprise a fourth layer wherein the fourth layer comprises a polymer. In another embodiment, the fourth layer may comprise a copolymer. In one example, the copolymer is poly (di (ethylene glycol) methylether methacrylate)-co-polyacrylic acid or PDEGMA-co-PAA. In other examples, first layer comprises poly (L-lysine) and the second layer comprises a copolymer PDEGMA-PAA. In still other example, first layer comprises poly (ethylene imine) and the second layer comprises PDEGMA-PAA.

In some embodiments, the cell culture support may comprise a homopolymer layer. Non-limiting examples of homopolymers include poly (L-lysine), poly (allylamine), poly (ethylene imine) and poly (vinylpyrrolidone). The homopolymer may be responsive to ionic strength or pH. The change in ionic strength or pH of the environment of the homopolymer layer may change its chemical structure. For example, poly-L-lysine (PLL) contains a pH responsive amino group, which can be deprotonated (hydrophobic) or protonated (hydrophilic). Addition of phosphate buffered saline (PBS) may facilitate the dissolution of the multilayer system made of TRABC and PLL due to the ionic interaction of chloride or phosphate anions with positively charged lysine moieties of PLL and sodium cation with carboxylic groups of TRABC.

In one embodiment, the homopolymer or copolymer may further be functionalized with an additional fluorescent probe. For example, the fluorescent probe may be fluorescein 5-isothiocyanate (FITC). Introduction of a fluorescent probe enables measurement of fluorescence intensity of the homopolymer or copolymer layer to determine proper formation of multilayer coatings.

In some embodiments, a polymer layer is disposed between two copolymer layers. In one embodiment, a homopolymer layer is disposed between two copolymer layers. In another embodiment, a copolymer layer is disposed between two homopolymer layers. In some other embodiments, there may be several alternating layers of the homopolymer layer and the copolymer layer. In some embodiments, interaction between homopolymer layer and the copolymer layer may be non-covalent. A non-covalent interaction, for example, can be ionic interaction, electrostatic interaction, hydrophobic interaction, Van der Waals interaction or dipole-dipole interaction. The homopolymer may interact electrostatically with the copolymer layer.

Coating of the substrate with polymers via non-covalent interactions has significant advantages. For example, the cell culture support coated with dual stimuli responsive copolymer has the flexibility to accommodate complex substrate geometries, including, for example, flat sheets, beads, cubes, porous foams, fibers and nonwovens.

Exemplary embodiments of the cell culture support of the invention are schematically shown in FIG. 1. A glass slide 2 coated with a homopolymer coating 4 is illustrated in FIG. 1A. A glass slide 2 coated with a homopolymer coating 4 and a copolymer coating 6 is illustrated in FIG. 1B. A glass slide 2 coated with four layers of homopolymer and copolymer in an alternating fashion is illustrated in FIG. 1C. A glass slide 2 coated with eight layers of homopolymer (4) and copolymer (6) in an alternating fashion is illustrated in FIG. 1D. In some specific embodiments, the homopolymer layer is Poly (L-Lysine) (PLL) and the copolymer layer is TRABC.

Figure 2C:
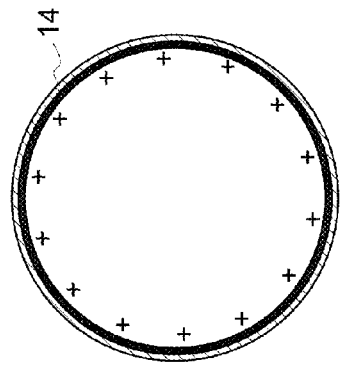
FIGS. 2A to 2F are schematic representations of uncoated or single layer TRABC coated or multilayer TRABC/PLL coated Cytodex 1™ microcarriers.
Figure 2D:
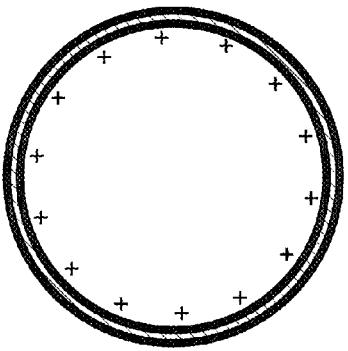
Figure 2B:
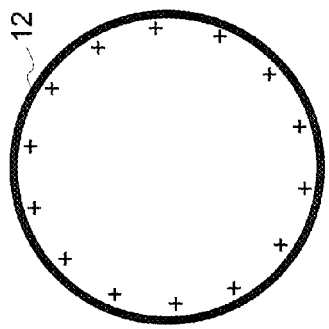
Figure 2E:
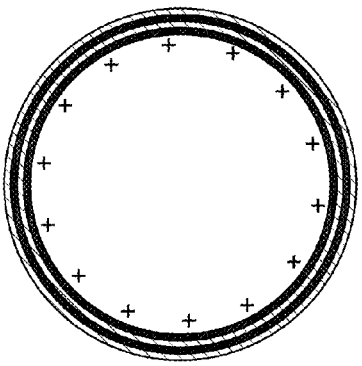
Figure 2A:
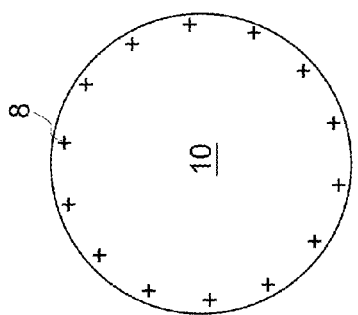

An uncoated Cytodex 1™ microcarrier bead is illustrated as FIG. 2A. A Cytodex 1™ microcarrier bead coated with TRABC is illustrated as FIG. 2B. A Cytodex 1™ microcarrier bead coated with TRABC and PLL is illustrated as FIG. 2C. A Cytodex 1™ microcarrier bead coated with three layers of TRABC and PLL in an alternating fashion is illustrated as FIG. 2D. A Cytodex 1™ microcarrier bead coated with four layers of TRABC and PLL in an alternating fashion is illustrated as FIG. 2E. A Cytodex 1™ microcarrier bead coated with five layers of TRABC and PLL in an alternating fashion is illustrated as FIG. 2F. Here, element 8 represents the positively charged surface of Cytodex 1™ (e.g. containing diethyl amino ethyl groups), element 10 is the crosslinked dextran matrix of the bead, element 12 is TRABC, and element 14 is PLL.

Some embodiments of the methods of the invention for culturing cells, comprise the steps of providing a cell culture support. The cell culture support may comprise a dual stimuli responsive copolymer immobilized on a substrate, wherein the dual stimuli responsive copolymer has a lower critical solution temperature in a range from about 10° C. to 37° C. The dual stimuli responsive copolymer is further pH responsive in a pH range from about 3 to 10. The method includes culturing of cells on the cell culture support. In one embodiment, the cells may be cultured at a temperature lower than LCST. In some other embodiment, the cells may grow at a temperature in a range from about 0° C. to 37° C. In another embodiment, the cells may grow at a temperature in a range from about 0° C. to 20° C. In a specific embodiment, the cells may grow at a temperature in a range from about 10° C. to 20° C.

The cells may be grown in a culture flask and may be added to the cell culture support for further growth. Cells may be grown on the cell culture support after extraction from blood, bone marrow or tissue section. In some other embodiments, the cell culture support may be introduced in a spinner flask, a stacked culture flask, a stirred tank reactor, or any other in-vitro cell culture system.

In one embodiment, cells may release from cell culture support by altering ionic strengths or pH of a solution that is in contact with the cell culture support. As the cell culture support comprises a homopolymer layer responsive to ionic strength or pH, cell release may be enhanced by changing these two parameters separately or by changing these two parameters simultaneously. In another embodiment, as the copolymer of cell culture support is pH responsive, cells may be released by using solutions of varying pH. In yet another embodiment, cells may be released from cell culture support by changing the temperature of the support.

The cell culture support provided herein may be effectively used to grow delicate cells such as stem cells. Stem cells are characterized by their ability to self-renew and to differentiate into a diverse range of cell types. Stem cells may now be grown and transformed into specialized cells with characteristics consistent with cells of various tissues such as muscles or nerves through cell culture. Adult stem cells may be obtained from a variety of sources, including umbilical cord blood and bone marrow, and are being used in medical therapies. Embryonic stem cells have also been proposed as promising candidates for future therapies. Culture and release of stem cells with high purity, high efficiency and high yield are becoming a clinical as well as a research need. This requirement may be addressed by using the thermoresponsive copolymer based cell culture support of this invention.

Some embodiments of the kit of the invention, for culturing cells, comprises: a cell culture support having a substrate, a dual stimuli responsive block copolymer immobilized on a substrate, and wherein the dual stimuli responsive block copolymer is both thermoresponsive and pH responsive; and may further comprise culture media suitable for cell growth. The kit may comprise cells in a frozen condition and may further comprise a protocol for using the cell culture support. A manual may include protocols for handling cells and for culturing and releasing cells.

EXAMPLE 1

Synthesis of PDEGMEMA-co-PAA

PDEGMEMA-co-PAA was synthesized and characterized using standard techniques. The synthesis of PDEGMEMA-co-PAA included three steps, (Scheme 1) polymerization of DEGMEMA, copolymerization of PDEGMEMA with t-butylacrylate, and selective hydrolysis of the copolymer PDEGMEMA-P(tBA) to form desired copolymer PDEGMEMA-co-Poly (acrylic acid) (PDEGMEMA-co-PAA).

Scheme 1 for synthesis of thermoresponsive amphiphilic block copolymer (TRABC) is shown below.

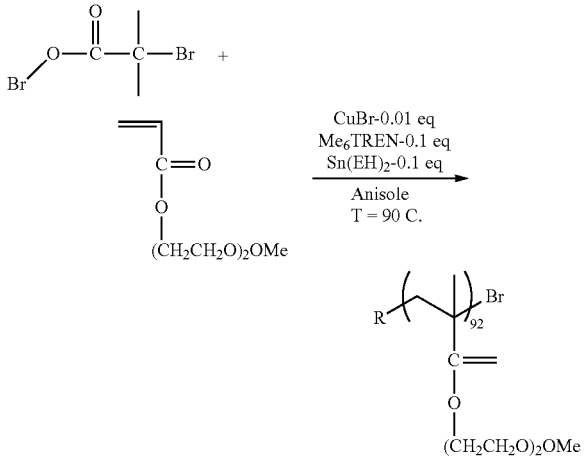

Scheme 1. Synthesis of PDEGMEMA-co-PAA

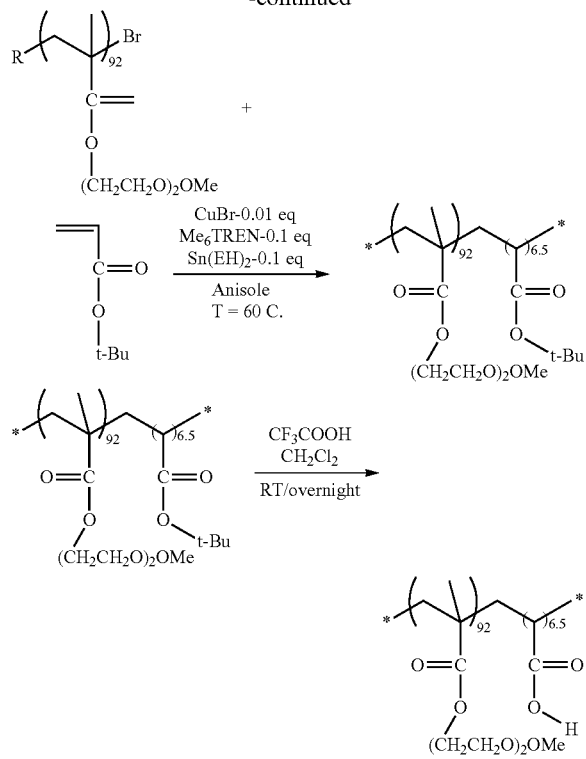

Polymerization of DEGMEMA: Polymerization was done in a 25 ml Schlenk flask equipped with magnetic stir bar. The Schlenk flask was filled with 9.18 g (0.0488 mol) of monomeric DEGMEMA and 71.3 mg (366.8 umol) of ethyl 2-bromoisobutyrate. The reaction mixture was de-aired via nitrogen purge for 30 min Subsequently, 24.24 umol of CuBr/Me6TREN complex in anisole was added followed with an additional 36.58 umol of Me6TREN and 36.58 umol of Sn(EH)$_2$ to the reaction mixture. The flask was placed into a 90° C. oil bath to start the polymerization reaction. Monomer conversion was followed by gas phase chromatography (GC). The reaction was stopped at the time of 60% monomer to polymer conversion. The polymer Poly (DEGMEMA) or PDEGMEMA) was precipitated by rapid addition of the polymer solution to 1 L of cold hexane. Precipitated white sticky flakes were dissolved in THF and re-precipitated in hexane. The collected polymer was dried in vacuum to yield 4.5 g of white, sticky solid.

Copolymerization of PDEGMEMA with t-butylacrylate (t-BA): A 50 ml Schlenk flask was filled with 4.82 g (327.7 umol) of PDEGMEMA, 10 ml of anisole and 1.05 g (0.082 mol) of t-BA. The reaction mixture was de-aired by three consecutive procedures of freeze, vacuum and thaw. Subsequently, 213.6 mg (0.82 μmol) of CuBr/Me6TREN complex in anisole was added followed by addition of 32.72 μmol of Me6TREN and 32.72 μmol of Sn(EH)$_2$. The flask was placed into 50° C. oil bath to start the polymerization reaction. Monomer conversion was followed by GC analysis. The reaction was stopped at about 40% conversion of monomer to polymer product and the polymer was precipitated by rapid addition of the reaction mixture to 1 L of cold hexane. The precipitated white sticky flakes were dissolved in THF and re-precipitated in hexane. The collected polymer was dried in vacuum to yield 3.5 g of white sticky solid.

Figure 3:
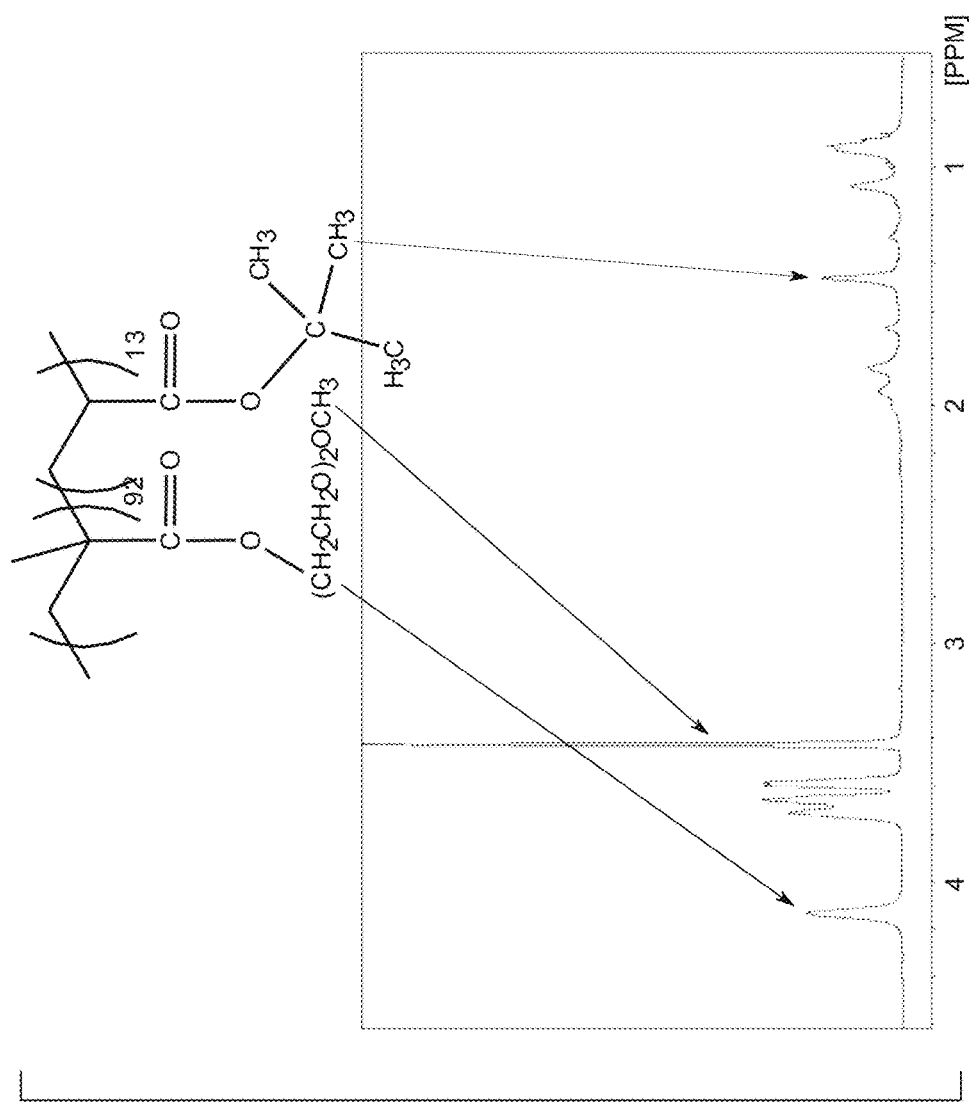
FIG. 3 is a $H^1$ NMR spectrum of poly (di (ethylene glycol) methylether methacrylate) (PDEGMEMA) block copolymer with poly (tertiary butyl acrylate) (Pt-BA).

Selective Hydrolysis of the PDEGMEMA-co-Poly(tBA) to Copolymer PDEGMEMA-PAA: Selective hydrolysis of t-butyl ester groups of PDEGMEMA-co-P(tBA) was accomplished by treatment of PDEGMEMA-co-P(tBA) with an excess of anhydrous trifluoroacetic acid in dichloromethane following a procedure described in J. Polym Sci., Part A, Polym. Chem., 2000, 38, 4805 by K. Wooley et al. 3.3 g of PDEGMEMA-co-P(tBA) and 10 ml of dichloromethane were added to a 50 ml two-necked flask equipped with magnetic stir bar. The mixture was stirred for 30 min to dissolve the polymer. Subsequently, 7.5 g (65 mmol) of trifluoroacetic acid was added drop-wise and the mixture was stirred at room temperature over night (16 hrs). The hydrolysis of ester group was followed by $^1$H NMR spectroscopy where the disappearance of the signal at 1.49 ppm and formation of the sharp singlet peak at 1.62 ppm implied the conversion of t-Butyl ester groups to t-butyl trifluoroacetate. The reaction was stopped at about 80% conversion of t-butyl ester group. Solvent and excess trifluoroacetic acid was removed by overnight treatment of air while the air was flowing gently through the flask. The sticky solid was dissolved in 5 ml of THF and was purified by dialysis against de-ionized (DI) water with pH 8 (adjusted by 0.1N NaOH), using 7000 MW cut-off dialysis tubes, for 2 days. The dialysis was continued in pure DI water (pH ~7) for additional 3 days. The resulting solution was transferred to plastic centrifuge tubes and was freeze-dried to yield a white sticky solid. $^1$H NMR was performed to characterize the polymer and the results are illustrated in FIG. 3.

Dynamic Light Scattering (DLS) Analysis

Figure 4A:
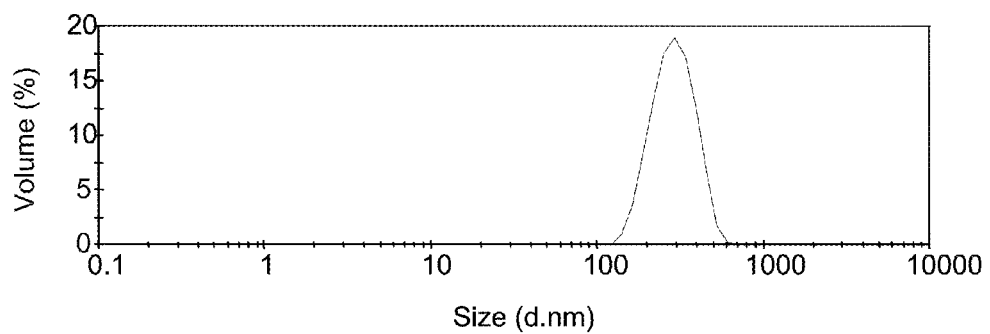
FIGS. 4A and 4B are dynamic light scattering (DLS) graphical plots showing the effect of temperature on size distribution of particles or aggregates (measured as hydrodynamic radius).
Figure 4B:
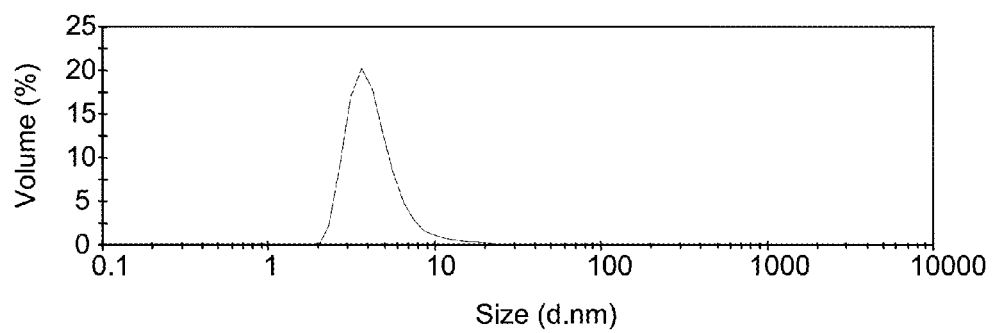

Dynamic Light Scattering (DLS) was performed to characterize the thermoresponsive property of the synthesized copolymer, PDEGMEMA-co-PAA. The thermoresponsive behavior of this polymer was clearly observed in water. A solution (0.1 wt/vol %) of TRABC in DI water at pH 2 became cloudy above 26° C. and the observed cloudiness disappeared when the solution was cooled down to 24° C., as the process was reversible (FIGS. 4A and 4B). Dynamic light scattering (DLS) measurements indicated the formation of large aggregates (having a diameter of ~200 nm) at temperature above 26° C. (here 32° C.) (FIG. 4A), which undergo de-agglomeration (having a diameter of ~20 nm) at a temperature below 26° C. (here, 20° C.) (FIG. 4B), as shown in FIG. 4.

The effects of pH on the aggregation of TRABC in DI water were observed in different examples. Dynamic Light Scattering (DLS) studies were carried out using 0.05% solution of TRABC in DI water. The pH was adjusted by addition of 1 drop of 0.1N HCl or 0.1N NaOH. The results of DLS studies are summarized in FIG. 5A to 5D. The DLS results clearly indicate that at high pH (above pH 9) and temperature below LCST (26° C.), the TRABC polymer behaves as a typical polyelectrolyte and is completely soluble (particle having a diameter of 10 nm) (FIG. 5A). The increase of temperature to 30° C. leads to formation of micelles with particle size about 92 nm (FIG. 5B). The reduction of pH from pH 10 to pH 2 at 30° C. causes polymer precipitation (FIG. 5D). Finally, the precipitated polymer goes back to solution and forms micelles when the temperature is reduced to 24° C. (FIG. 5C). However, the size of the formed micelles is significantly larger (having a diameter of 260 nm) at pH 2 than the micelles formed at high pH (~10) and temperature above LCST.

EXAMPLE 2

Figure 1C:
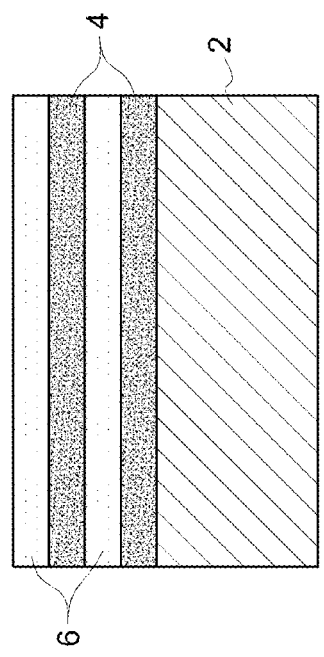
Figure 1D:
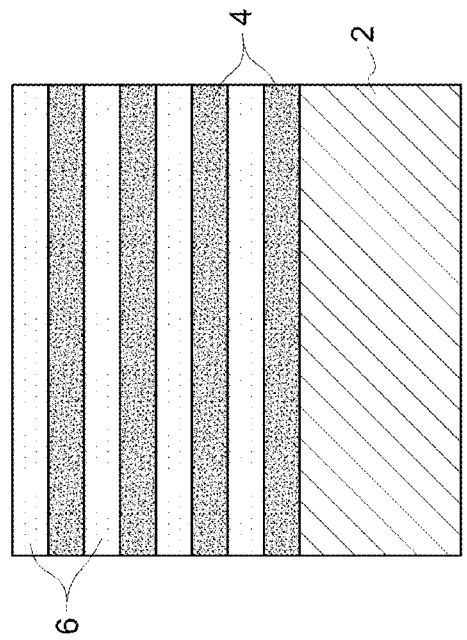

Different samples of single layer or multi-layer coated cell culture supports as illustrated in FIGS. 1A to 1D were prepared. The method of preparation of the coated glass slides for culturing cells are described herein. Poly-L-Lysine (PLL) coated glass slides (Polysciences Inc.) were diced into 8×8 mm squares and were consecutively washed with DI water and with absolute ethanol followed by air-drying at room temperature. The dry slides (FIG. 1A) were immersed into 0.1% solution of TRABC in DI water at 37° C. for 60 minutes. Subsequently, the slides were washed by immersion in two baths with DI water and a few of these slides (FIG. 1B) were dried and used for cell culture. The remaining slides were incubated in 0.1% solution of Poly-L-Lysine (Aldrich). The solution of poly-L-Lysine (PLL) contained a small amount of poly-L-lysine functionalized with FITC fluorescent probe. The slides were kept in contact with PLL for 60 minutes at 37° C. Subsequently, the slides were washed with warm (37° C.) DI water (two baths) and transferred back into 0.1% solution of TRABC. After 60 minutes of exposure to TRABC at 37° C., the slides were washed with warm DI water. Some of these slides were dried and used for cell culture (FIG. 1C). Rest of the slides were subjected consecutively to the 0.1% solution of poly-L-Lysine and then to 0.1% TRABC to form additional four layers of PLL/TRABC/PLL/TRABC on the surface (FIG. 1D). The amount of deposited PLL was determined by measurement of fluorescence. The fluorescence was measured on a Typhoon™ fluorescence imager (GE Healthcare).

Figure 6:
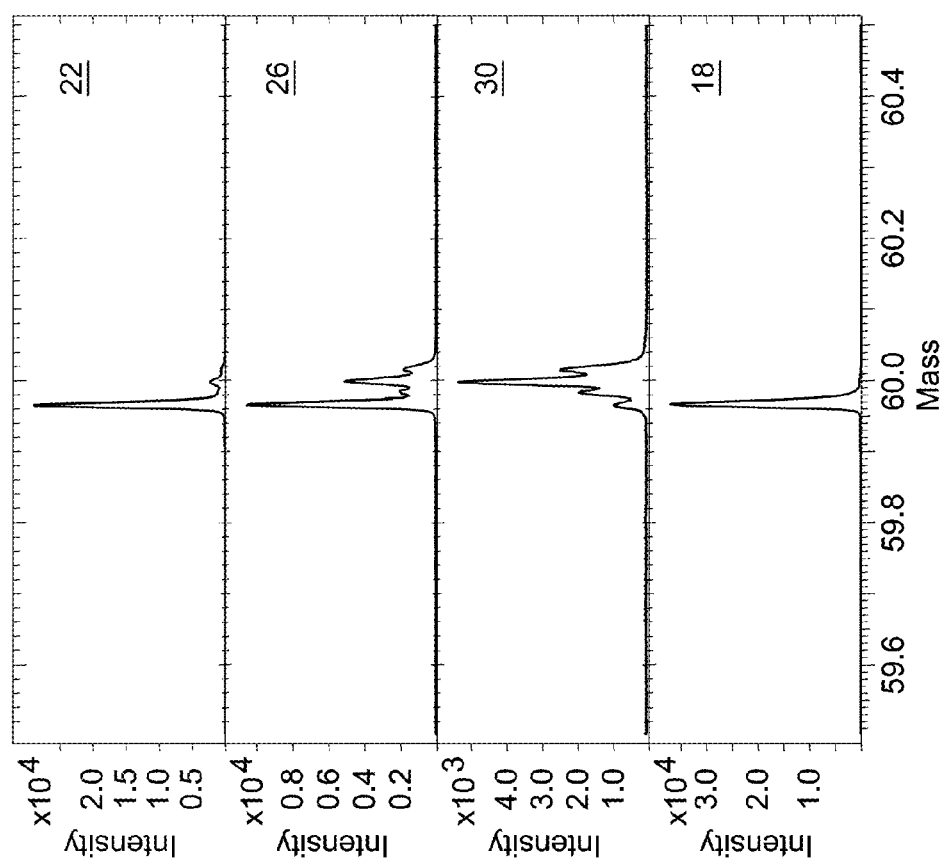
FIG. 6 represents a series of graphical plots illustrating Time of Flight Secondary Ion Mass Spectrometry (ToF-SIMS) analysis of PLL or TRABC coated glass slides.

Quantitative analysis of the observed fluorescence confirmed the formation of glass/PLL/TRABC two-layer coating (FITC bound), four-layer coating (FITC bound) and eight-layer coating (FITC bound). The fluorescence results were additionally confirmed by ToF SIMS analysis (FIG. 6). The ToF SIMS spectra showed a gradual change in the peak height and peak position for observed negative $SiO_2$ ions. The layer-by-layer (LBL) coating of samples having eight PLL/TRABC layers is thick enough that $SiO_2$ ions are almost undetectable (FIG. 6, graphs 22, 26 and 30 for two layer, four layer and eight layer coated glass slides respectively) with respect to the glass substrate shown in FIG. 6, graph 18 for uncoated glass slide.

FIG. 7A is a two-dimensional ToF-SIMS image analysis of negative ions of an example of a glass slide coated with two layers of PLL/TRABC and FIG. 7B is a two-dimensional image analysis of ToF-SIMS negative ions of an example of a glass slide coated with eight alternating layers of PLL/TRABC. The concentration of $C_2HO$ (32), $C_3H_3O$ (34), $C_4H_5O_2$ (36), $SiO_2$ (38), $SiHO_3$ (40) ions and total ions (42) for a two-layer system, (one layer of TRABC) did not, in this example, coat the glass/PLL surface evenly, as shown in FIG. 7A. The deposited TRABC seemed to first form small islands on the surface (FIG. 7A). The deposition of the additional PLL/TRABC layers leads to a more uniform coating, which is thick enough to diminish the presence of negative ions related to glass (FIG. 7B). The concentration of $C_2HO$ (44), $C_3H_3O$ (46), $C_4H_5O_2$ (48), $SiO_2$ (50), $SiHO_3$ (52) ions and total ions (54) for an eight-layer system, (four layer of TRABC) coat the glass/PLL surface evenly, is shown in FIG. 7B. It should be noted that the quality and coverage of the coatings can be adjusted by varying the substrate and polymer structure, and the deposition conditions such as the concentration, time and temperature.

Cell Culture and Release

The prepared cell culture support samples were used to culture and release CHO (Chinese Hamster Ovary, ATCC) and MRC-5 (human lung fibroblast, ATCC) cells. These cells were routinely cultured on polystyrene surfaces using the following media: F-12K (EMEM, Invitrogen) and 10% FBS (fetal bovine serum); and Eagle's minimum essential medium (EMEM, Invitrogen) and 10% FBS supplemented with 100 U/mL penicillin-streptomycin (P/S, Invitrogen). Culture methods were performed at 37° C., in a humidified atmosphere of 5% $CO_2$. Cells were passaged by performing the steps of briefly rinsing the cell layer with PBS (phosphate buffered saline) followed by addition of 3.0 ml of 0.25% (w/v) Trypsin and 0.53 mM EDTA solution to the culture flask and observing the cells in an inverted microscope until the cell layer is dispersed. Subsequently, 7 ml of complete growth medium was added to the cells and the media and the cells were mixed by gently pipetting several times. Appropriate aliquots of the cell suspension were transferred to new culture vessels with fresh media. Cell culture methods were performed with samples of FIG. 1A (PLL coated glass slide) and FIG. 1C (four layer of PLL/TRABC coated glass slide). Coated glass sections (1 cm×1.2 cm) were sterilized by washing with 70% EtOH, and were allowed to air dry before being hydrated in warm cell culture medium and seeded with recently trypsinized cells at ~30% confluence.

Figure 9A:
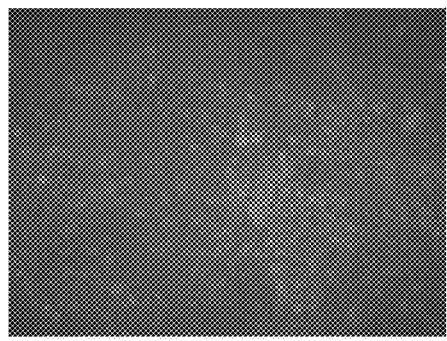
FIGS. 9A to 9D are 100× optical microscopy images of slides illustrating cell growth and cell release for MRC-5 cells.
Figure 9C:
Figure 9B:
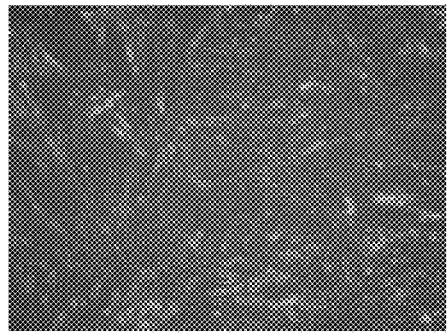
Figure 9D:
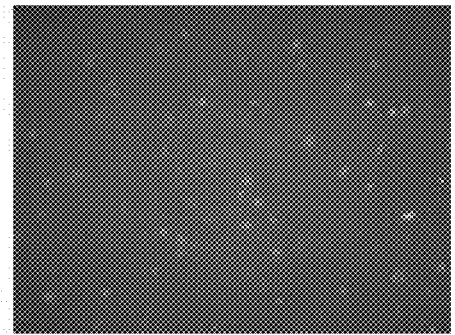

Cultures were allowed to proliferate overnight in cell culture incubators and thermal release tested after approximately 24 hours of cell growth by cooling the cultures to 4° C. for 10 min FIG. 8A; 8C show the cell growth on the PLL coated cell culture supports and PLL/TRABC (eight layers) coated cell culture support for CHO cells. FIGS. 8B, 8D show the PLL coated cell culture supports and PLL/TRABC (eight layers) coated cell culture supports after CHO cell release by cooling (at 4° C.) and washing of the cell culture support. FIGS. 9A, 9C show MRC-5 cell growth on the PLL coated cell culture supports and PLL/TRABC (eight layers) coated cell culture support. FIGS. 9B, 9D show the PLL coated cell culture supports and PLL/TRABC (eight layers) coated cell culture supports after MRC-5 cell release by cooling (at 4° C.) and washing of the cell culture support. It is also important to note that the morphology of the cells grown on the control surface (FIGS. 8A and 9A) is indistinguishable from those grown on the TRABC coated glass surface (FIGS. 8C and 9C) at 37° C.

Figure 10:
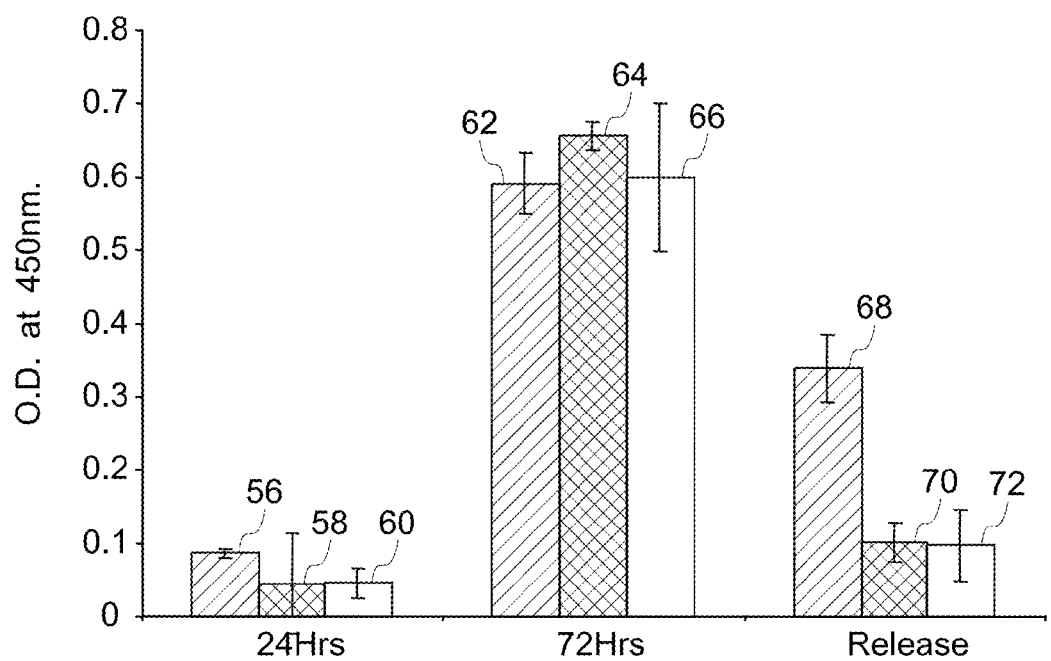
FIG. 10 is a bar graph representing the number of cultured cells present on the coated slides after cell growth or after cell release.

The quantitative measurement of cell growth and cell release is presented in FIG. 10 by measuring the optical density of the cell proliferation assay solution at 450 nm using WST-1 assay reagent. Cell growth on PLL coated glass slides (bar 56), four layers of TRABC/PLL coated glass slides (bar 58) and eight layers of TRABC/PLL coated glass slides (bar 60) after 24 hr are shown in FIG. 10, first grouping. Cell growth on PLL coated glass slides (bar 62), four layers of TRABC/PLL coated glass slides (bar 64) and eight layers of TRABC/PLL coated glass slides (bar 66) after 72 hr are shown in FIG. 10, second grouping. Number of cells present on coated glass slides (bar 68), four layers of TRABC/PLL coated glass slides (bar 70) and eight layers of TRABC/PLL coated glass slides (bar 72) after cell release are shown in FIG. 10, third grouping. Therefore, FIG. 10 shows three different samples (PLL coated, four layers of TRABC/PLL coated and eight layers of TRABC/PLL coated) having comparable cell growth after 72 hr whereas bars 70 and 72 showed efficient cell release for the four layers of TRABC/PLL coated and eight layers of TRABC/PLL coated glass slides. Bar 68 is a PLL coated glass slide served as a control, which is not showing cell release. The difference between the signal for cell growth at 72 hr and signal for cell release gives a measure of the release efficiency, which is clearly good in the 4- and 8-layer TRABC/PLL coated glass slides, but not so much in the control.

EXAMPLE 3

The copolymer is applied on to the substrate of the device (cell culture support) as a single layer or in multi-layers, and a non-limiting example of a substrate is Cytodex microcarrier beads (Cytodex 1™). Different examples of single layer or multi-layer coatings are described in FIGS. 2A to 2F. The method of preparation of the coated Cytodex microcarrier beads for culturing cells is described here.

In one example, TRABC is applied on to the microcarrier beads (Cytodex 1™). Cytodex 1™ microcarriers (FIG. 2A), which are positively charged particles having diameter of ~180 microns with diethyl aminoethyl (DEAE) functionality, were coated with TRABC (FIG. 2B), and were tested for cell growth and temperature-triggered facile cell release. Cytodex 1™ was functionalized with TRABC (FIG. 2B) by the following method. 1 ml of 0.5 wt/vol % of TRABC in DI water was added to 10 ml of 0.1 wt/vol % suspension of Cytodex 1™ microcarriers in DI water and the solutions were gently mixed at 37° C. for 24 hrs. The resulting suspension can be stored for a long time at 4° C. Before starting the cell culture experiment, the functionalized Cytodex 1™ microcarriers were separated from excess TRABC by washing with warm 1×PBS (Phosphate buffered saline). The resulting suspension of the functionalized Cytodex 1™ microcarriers in PBS was used for the cell culture experiments.

Figure 2F:
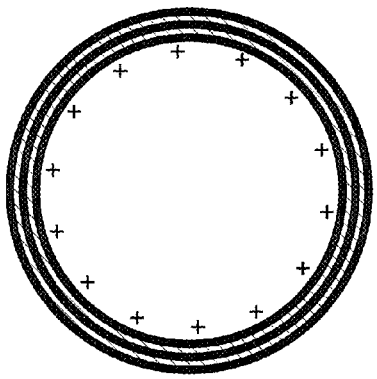

In another example, the Cytodex 1™ microcarriers were functionalized with multi-layer coating of TRABC and poly L-lysine (PLL) as presented in FIG. 2C (two layers of TRABC/PLL), FIG. 2D (three layers of TRABC/PLL/TRABC), FIG. 2E (four alternating layers of TRABC/PLL) and FIG. 2F (five alternating layers of TRABC/PLL). The coating was prepared by simple dispersion of Cytodex 1™ in 0.1% solution of TRABC in water for 1 hr, which was followed by centrifugation (2 min at 500 G), washing with DI water and exposure to 0.1% solution of PLL in DI water. The above procedure was repeated 3 times and finished with a final coating of TRABC (shown in FIG. 2). These functionalized Cytodex 1™ beads were tested for cell growth and release with CHO cells, and growth curves (obtained using proliferation assays, data not shown) were compared against uncoated Cytodex 1™ microcarrier (FIG. 2A).

FIG. 11A shows the coverage of CHO cells at 37° C. on the uncoated Cytodex 1™. FIG. 11C shows the coverage of CHO cells at 37° C. on monolayer (TRABC) coated Cytodex 1™. FIG. 11B shows the extent of cell release at 4° C. from uncoated Cytodex 1™ and FIG. 11D shows the extent of cell release at 4° C. from a monolayer of TRABC coated Cytodex 1™. Beads were pre-incubated with medium containing 100% FBS. The plates containing beads were left at 4° C. and examined after one hour, at which point they have released quite well from the TRABC-coated beads. Residual cells present on the Cytodex 1™ beads were imaged. Cell growth on uncoated Cytodex 1™ and on monolayer of TRABC coated Cytodex 1™ is seen in FIGS. 11A and 11C respectively. The images after cell release from uncoated Cytodex 1™ and from monolayer of TRABC coated Cytodex 1™ are seen in FIGS. 11B and 11D respectively. These images represent more efficient cell release from TRABC coated Cytodex 1™ (FIG. 11D) with respect to the uncoated Cytodex 1™ (FIG. 11B).

For another example, multilayer coated Cytodex 1™ beads were prepared. FIGS. 12A to 12D show the coverage of CHO cells at 37° C. and cell release at 4° C. on uncoated cytodex and on five-layer of TRABC/PLL coated Cytodex 1™. Beads were pre-incubated with medium containing 100% FBS. The plates containing beads were left at 4° C. and examined after one hour, at which point cells have released quite well from the TRABC-coated beads. Residual cells present on the Cytodex 1™ beads were imaged for the uncoated Cytodex 1™ and for the five-layers of TRABC/PLL coated Cytodex 1™. Cell growth for the uncoated Cytodex 1™ and for the five-layer TRABC/PLL coated Cytodex 1™ is seen in FIGS. 12A and 12C and the beads after cell release for uncoated Cytodex 1™ and for five-layer of TRABC coated Cytodex 1™ is seen in FIGS. 12B and 12D, which shows higher cell release efficiency from multilayer TRABC coated Cytodex 1™ (FIG. 12D) as compared to uncoated Cytodex 1™ (FIG. 12B).

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A cell culture support comprising:
    a substrate;
    a first coat immobilized on the substrate via non-covalent interaction, wherein the first coat comprises a homopolymer; and
    a second coat immobilized on the first coat via non-covalent interaction, wherein the second coat comprises a dual stimuli responsive copolymer, and wherein the dual stimuli responsive copolymer is a block copolymer comprising poly(di(ethyleneglycol) methylether methacrylate)-co-polyacrylic acid.

2. The cell culture support of claim 1, wherein the homopolymer is responsive to pH and/or ionic strength.

3. The cell culture support of claim 1, wherein the homopolymer is selected from a group consisting of poly-L-lysine, poly-allylamine, poly-ethyleimine, and poly-vinylpyrrolidone.

4. The cell culture support of claim 1, wherein the homopolymer comprises poly-L-lysine.

5. The cell culture support of claim 4, further comprising a third coat immobilized on the second coat and a fourth coat immobilized on the third coat, wherein the third coat comprises a homopolymer and the fourth coat comprises a dual stimuli responsive copolymer.

6. The cell culture support of claim 5, wherein the third coat comprises poly-L-lysine.

7. The cell culture support of claim 6, wherein the fourth coat comprises poly(diethyleneglycolmethylether methacrylate)-co-polyacrylic acid.

8. The cell culture support of claim 7, further comprising alternating coats of poly-L-lysine and poly(diethyleneglycolmethylether methacrylate)-copolyacrylic acid.

9. The cell culture support of claim 1, wherein the block copolymer has a lower critical solution temperature in a range from about 10° C. to about 37° C.

10. The cell culture support of claim 9, wherein the block copolymer is pH responsive in a pH range from about 3 to about 10.

11. The cell culture support of claim 1, wherein the substrate comprises a material selected from a group consisting of glass, polymer, metal, ceramic, and a combination thereof.

12. The cell culture support of claim 1, wherein the substrate comprises a microcarrier, a membrane, a fiber, a hollow fiber, a nonwoven fiber, a capillary, a vessel, a flask, a disc, a bead, a Petri dish, a plate, a fabric, a nano-fiber mat, a particle, a scaffold, or a foam.

13. The cell culture support of claim 12, wherein the microcarrier is a bead.

14. A cell culture support comprising:
    a substrate;

a first coat immobilized on the substrate via non-covalent interaction, wherein the first coat comprises a dual stimuli responsive copolymer, and wherein the dual stimuli responsive copolymer is a block copolymer comprising poly(di(ethyleneglycol)methylether methacrylate)-co-polyacrylic acid; and a second coat immobilized on the first coat via non-covalent interaction, wherein the second coat comprises a homopolymer.

15. The cell culture support of claim 14, wherein the homopolymer comprises poly-L-lysine.

16. The cell culture support of claim 15, further comprising a third coat immobilized on the second coat and a fourth coat immobilized on the third coat, wherein the third coat comprises poly-(di(ethyleneglycol)methylether methacrylate)co- polyacrylic acid and the fourth coat comprises poly-L-lysine.

17. The cell culture support of claim 16, further comprising alternating coats of poly(diethyleneglycolmethylether methacrylate)-co-polyacrylic acid and poly-L-lysine.

18. The cell culture support of claim 14, wherein the substrate comprises a microcarrier, a membrane, a fiber, a hollow fiber, a capillary, a vessel, a flask, a disc, a bead, a Petri dish, a plate, a fabric, a nonwoven fiber, a nano-fiber mat, a particle, a scaffold, or a foam.

19. The cell culture support of claim 18, wherein the microcarrier is a bead.

\* \* \* \* \*